US006293951B1

(12) United States Patent
Alferness et al.

(10) Patent No.: US 6,293,951 B1
(45) Date of Patent: Sep. 25, 2001

(54) LUNG REDUCTION DEVICE, SYSTEM, AND METHOD

(75) Inventors: Clifton A. Alferness, Redmond, WA (US); Richard Y. Lin, Redwood City; Wilfred E. Jaeger, Portola Valley, both of CA (US)

(73) Assignee: Spiration, Inc., Redmond, WA (US)

( * ) Notice: Subject to any disclaimer, the term of this patent is extended or adjusted under 35 U.S.C. 154(b) by 0 days.

(21) Appl. No.: 09/379,972

(22) Filed: Aug. 24, 1999

(51) Int. Cl.[7] ..................................................... A61F 11/00
(52) U.S. Cl. ................................................................ 606/108
(58) Field of Search ...................................... 604/246, 247, 604/249, 256, 48; 606/108, 200, 213, 217; 623/1.24, 1.26, 23.68, 1.25, 23.7

(56) References Cited

U.S. PATENT DOCUMENTS

| 2,981,254 | * | 4/1961 | Vanderbilt | 604/246 |
|---|---|---|---|---|
| 3,657,744 | * | 4/1972 | Ersek | 606/153 |
| 3,788,327 | * | 1/1974 | Donowitz et al. | 604/247 |
| 3,874,388 | * | 4/1975 | King et al. | 606/213 |
| 4,852,568 | * | 8/1989 | Kensey | 606/213 |
| 4,968,294 | * | 11/1990 | Salama | 604/247 |
| 5,061,274 | * | 10/1991 | Kensey | 606/213 |
| 5,306,234 | * | 4/1994 | Johnson | 604/49 |
| 5,352,240 | * | 10/1994 | Ross | 623/2 |
| 5,366,478 | * | 11/1994 | Brinkerhoff et al. | 604/256 |
| 5,409,019 | * | 4/1995 | Wilk | 128/898 |
| 5,645,565 | * | 7/1997 | Rudd et al. | 606/213 |
| 5,800,339 | * | 9/1998 | Salama | 604/247 |
| 5,855,597 | * | 1/1999 | Jayaraman | 623/1 |
| 5,855,601 | * | 1/1999 | Bessler et al. | 623/2 |
| 5,944,738 | * | 8/1999 | Amplatz et al. | 606/213 |
| 5,947,997 | * | 9/1999 | Pavcnik et al. | 606/213 |
| 5,957,949 | * | 9/1999 | Leonhardt et al. | 606/108 |
| 5,976,174 | * | 11/1999 | Ruiz | 606/213 |
| 6,027,525 | * | 2/2000 | Suh et al. | 623/1 |
| 6,068,638 | * | 5/2000 | Makower | 606/159 |
| 6,077,291 | * | 6/2000 | Das | 606/213 |

FOREIGN PATENT DOCUMENTS

WO 98/48706 * 11/1998 (WO).

* cited by examiner

Primary Examiner—Gene Mancene
Assistant Examiner—Eduardo C. Robert
(74) Attorney, Agent, or Firm—Graybeal Jackson Haley LLP

(57) ABSTRACT

A device, system, and method provides for lung size reduction by permanently collapsing at least a portion of a lung. The lung portion may be collapsed by obstructing the air passageway which communicates the lung portion to be collapsed. The air passageway may be obstructed by an obstructing member which precludes airflow in either direction or with a one-way valve which permits air to be exhaled from the lung portion while precluding air from being inhaled into the lung portion. In addition, a vacuum may be pulled within the lung portion to be collapsed for collapsing the lung portion and while the lung portion is collapsed the obstructing member may be placed in the air passageway to maintain the lung portion in a permanently collapsed state.

23 Claims, 6 Drawing Sheets

LUNG REDUCTION DEVICE, SYSTEM, AND METHOD

BACKGROUND OF THE INVENTION

The present invention is generally directed to a device, system, and method for treating Chronic Obstructive Pulmonary Disease (COPD). The present invention is more particularly directed to such a device, system and method which provide lung size reduction without requiring invasive surgery.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia , and smooth muscle hypertrophy in terminal bronchioles.

The incidence, prevalence, and heath-related costs of COPD are on the rise. Mortality due to COPD is also on the rise. In 1991 COPD was the fourth leading cause of death in the United States and had increased 33% since 1979.

COPD affects the patient's whole life. It has three main symptoms: cough; breathlessness; and wheeze. At first, breathlessness may be noticed when running for a bus, digging in the garden, or walking up hill. Later, it may be noticed when simply walking in the kitchen. Over time, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled β-agonists. For those patients who respond poorly to the foregoing or who have persistent symptoms, pratropium bromide may be indicated. Further, courses of steroids, such as corticosterocds, may be required. Lastly, antibiotics may be required to prevent infections and influenza and pheumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopping reimbursing for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life.

Improvements in pulmonary function after LVRS have been attributed to at least four possible mechanisms. These include enhanced elastic recoil, correction of ventilation/perfusion mismatch, improved efficiency of respiratory muscaulature, and improved right ventricular filling.

Lastly, lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

In view of the foregoing, there in a need in the art for a new and improved therapy for COPD. More specifically, there is a need for such a therapy which provides more permanent results than pharmacotherapy while being less invasive and traumatic than LVRS. The present invention is directed to a device, system, and method which provide such an improved therapy for COPD.

SUMMARY OF THE INVENTION

The present invention provides a method of reducing the size of a lung including the step of permanently collapsing at least a portion of the lung. In accordance with a first embodiment, the lung may be collapsed by obstructing an air passageway communicating with the lung portion to be collapsed. The air passageway may be obstructed by placing an obstructing member in the air passageway. The obstructing member may be a plug-like device which precludes air flow in both directions or a one-way valve which permits air to be exhaled from the lung portion to be collapsed while precluding air from being inhaled into the lung portion. Once the air passageway is sealed, the residual air within the lung will be absorbed over time to cause the lung portion to collapse.

In accordance with a further embodiment of the present invention, the lung portion may be collapsed by inserting a conduit into the air passageway communicating with the lung portion to be collapsed, pulling a vacuum in the lung portion through the conduit to collapse the lung portion, and maintaining the lung portion in a collapsed state. The lung portion may be maintained in a collapsed state by sealing the air passageway with an obstructing member or by placing a one-way valve in the air passageway. To efficiently pull the vacuum in the lung portion to be collapsed, the space between the outer surface of the conduit and the inner surface of the air passageway may be sealed as the vacuum is pulled. Preferably, the air passageway is sealed while the lung portion is collapsed.

The present invention further provides a device for reducing the size of a lung. The device includes an obstructing member insertable into an air passageway communicating with a portion of the lung to be reduced in size and having an inner dimension. The obstructing member has an outer dimension for continuous contact with the air passageway inner dimension and sealing the air passageway upon placement in the air passageway for collapsing the portion of the lung and reducing the size of the lung. The obstructing member may be formed of resilient material so as to be collapsible for initial insertion into the air passageway in a collapsed condition and releasable to define the outer dimension upon placement in the air passageway. In accordance with a further embodiment of the present invention, the obstructing member may include a one-way valve to permit exhaled air to flow from the lung portion while precluding inhaled air from flowing into the lung portion.

The present invention further provides a system for reducing the size of a lung. This system includes a conduit configured to be passed down a trachea, into a bronchus communicating with the trachea, and into an air passageway communicating the bronchus with a lung portion to be reduced in size. The system further includes an obstructing member configured to be guided through the conduit into the air passageway for placement in the air passageway and sealing the air passageway for collapsing the lung portion. The conduit preferably has an outer dimension smaller than the inner dimension of the passageway and a sealing member seals the space between the conduit outer dimension and the air passageway inner dimension as the vacuum is pulled the system may further include a vacuum source for pulling a vacuum in the lung portion through the conduit prior to placement of the obstructing member. The sealing member may be an inflatable member. The conduit may include a first channel pulling the vacuum and for guiding the obstructing member into position and a second channel for inflating the inflatable sealing member.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

DETAILED DESCRIPTION OF THE PREFERRED EMBODIMENTS

Figure 1:
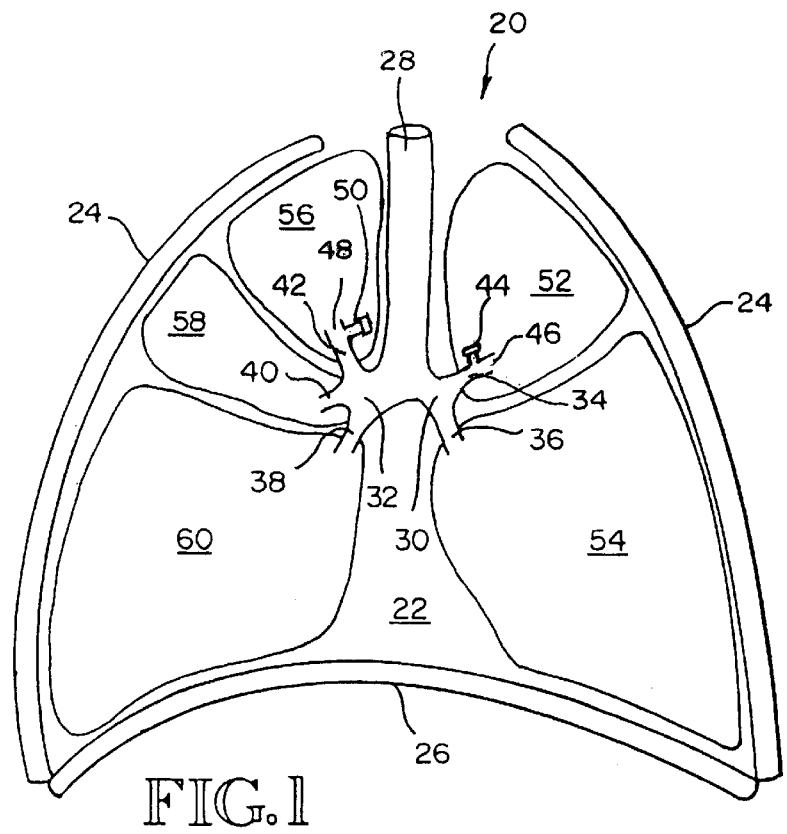
FIG. 1 is a simplified sectional view of a thorax illustrating a healthy respiratory system.

Referring now to FIG. 1, it is a sectional view of a healthy respiratory system. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, the bronchial branches 34, 36, 38, 40, and 42 and sub-branches 44, 46, 48, and 50. The respiratory system 20 further includes left lung lobes 52 and 54 and right lung lobes 56, 58, and 60. Each bronchial branch and sub-branch communicates with a respective different portion of a lung lobe, either the entire lung lobe or a portion thereof. As used herein, the term "air passageway" is meant to denote either a bronchial branch or sub-branch which communicates with a corresponding individual lung lobe or lung lobe portion to provide inhaled air thereto or conduct exhaled air therefrom.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax which in turn causes exhalation of the lung lobes.

Figure 2:
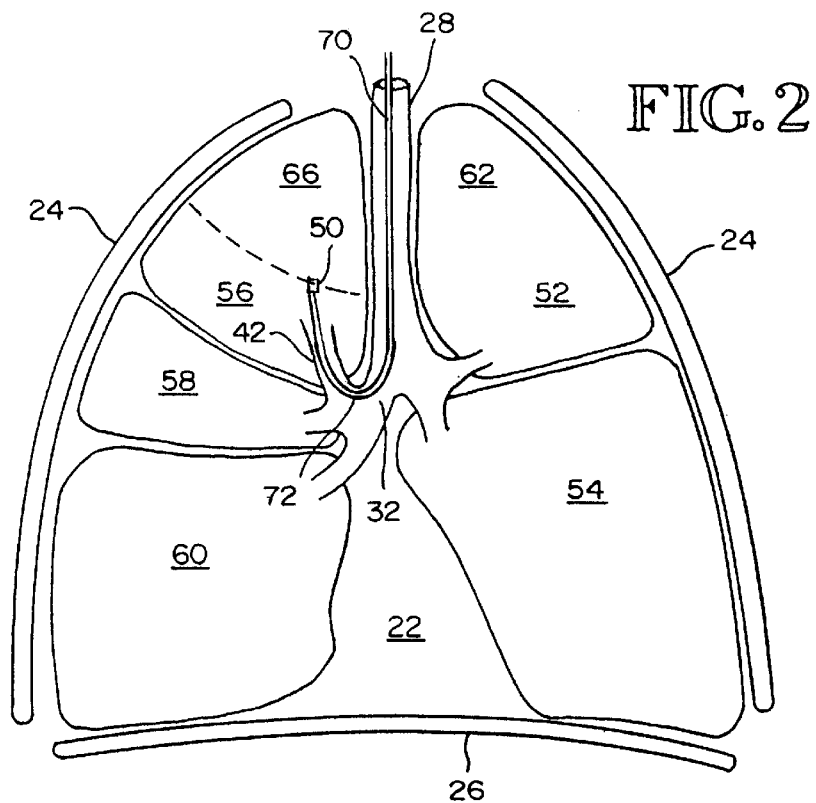
FIG. 2 is a sectional view similar to FIG. 1 but illustrating a respiratory system suffering from COPD and the execution of a first step in treating the COPD condition by reducing the size of a lung portion in accordance with the present invention.

In contrast to the healthy respiratory system of FIG. 1, FIG. 2 illustrates a respiratory system suffering from COPD. Here it may be seen that the lung lobes 52, 54, 56, 58, and 60 are enlarged and that the diaphragm 26 is not arched but substantially straight. Hence, this individual is incapable of breathing normally by moving the diaphragm 28. Instead, in order to create the negative pressure in the thorax 22 required for breathing, this individual must move the chest wall outwardly to increase the volume of the thorax. This results in inefficient breathing causing these individuals to breathe rapidly with shallow breaths.

It has been found that the apex portion 62 and 66 of the upper lung lobes 52 and 56, respectively, are most affected by COPD. Hence, the preferred embodiment will be described for treating the apex 66 of the right, upper lung lobe 56. However, as will be appreciated by those skilled in the art, the present invention may be applied to any lung portion without departing from the present invention.

The device, system, and method of the present invention treats COPD by deriving the benefits of lung volume reduction surgery without the need of performing lung volume reduction surgery. As will be seen hereinafter, the present invention contemplates permanent collapse of a lung portion or lung portions most affected. This leaves extra volume within the thorax for the diaphragm to assume its arched state for acting upon the remaining healthier lung tissue. As previously mentioned, this should result in improved pulmonary function due to enhanced elastic recoil, correction of ventilation/perfusion mismatch, improved efficiency of respiratory musculature, and improved right ventricle filling.

In accordance with this embodiment of the present invention, the COPD treatment is initiated by feeding a conduit or catheter 70 down the trachea 28, into the right mainstem bronchus 32, into the bronchial branch 42 and into and terminating within the sub-branch 50. The sub-branch 50 is the air passageway which communicates with the lung portion 66 to be treated.

The catheter 70 is preferably formed of flexible material such as polyethylene. Also, the catheter 70 is preferably preformed with a bend 72 to assist the feeding of the catheter from the right mainstem bronchus 32 into the bronchial branch 42.

Figure 3:
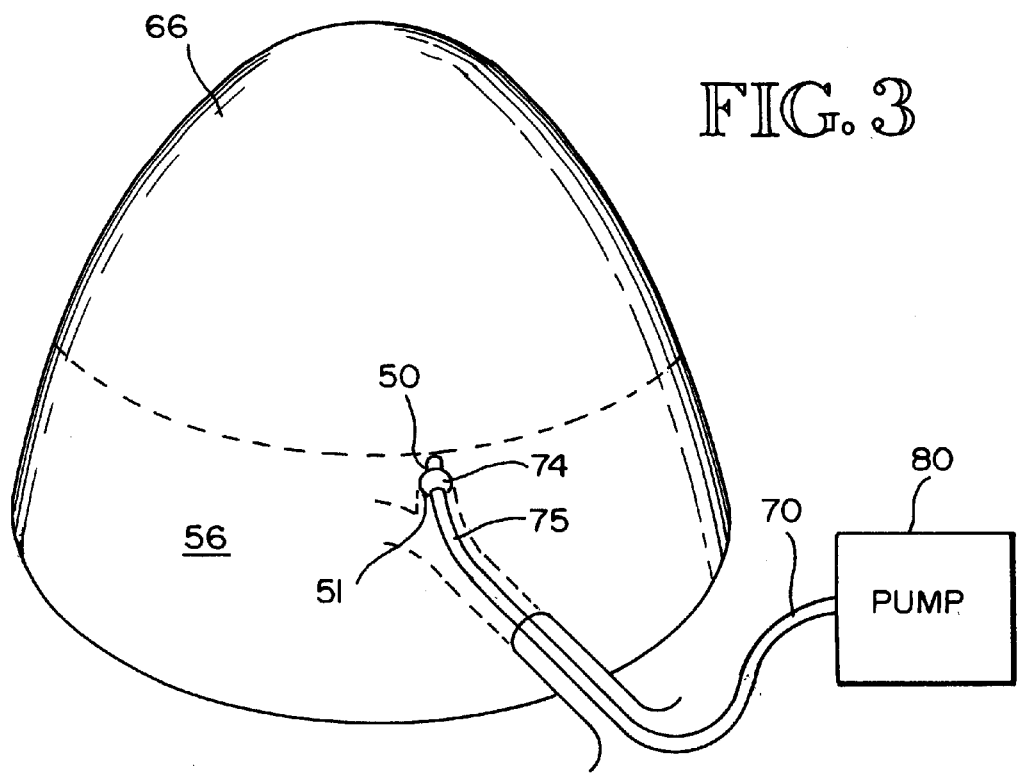
FIG. 3 is a perspective view, partly in section, and to an enlarged scale, illustrating an intermediate step in the treatment.
Figure 4:
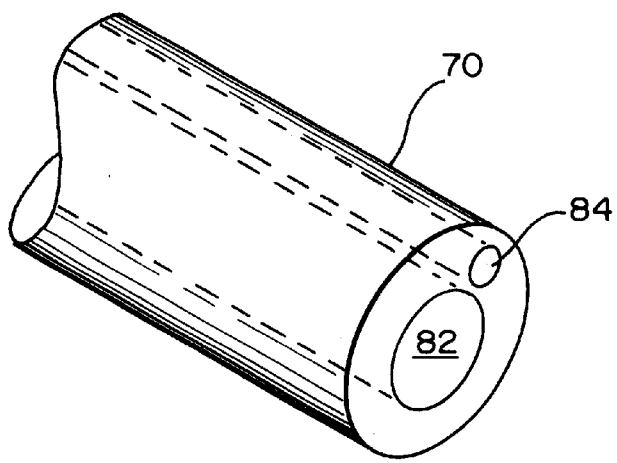
FIG. 4 is a partial perspective view of a conduit which may be utilized in practicing the present invention.

Referring now to FIG. 3, here it may be seen that the catheter includes an inflatable sealing member 74. The inflatable sealing member 74 is inflated within the sub-branch 50 to seal the space in-between the inner dimension 51 of the passageway 50 and the outer dimension 75 of the catheter 70. For inflating the inflatable member 74 and pulling a vacuum within lung portion 66, the catheter 70 is coupled to a pump 80. As may be seen in FIG. 4, the catheter 70 includes a main channel 82 through which the vacuum in lung portion 66 is pulled and a minor channel 84 which is utilized for inflating the inflatable member 74.

To establish the vacuum in lung portion 66, the inflatable member 74 is first inflated. Thereafter, the vacuum is pulled through the main channel 82 of the catheter 70 to pull the vacuum in lung portion 66.

Figure 5:
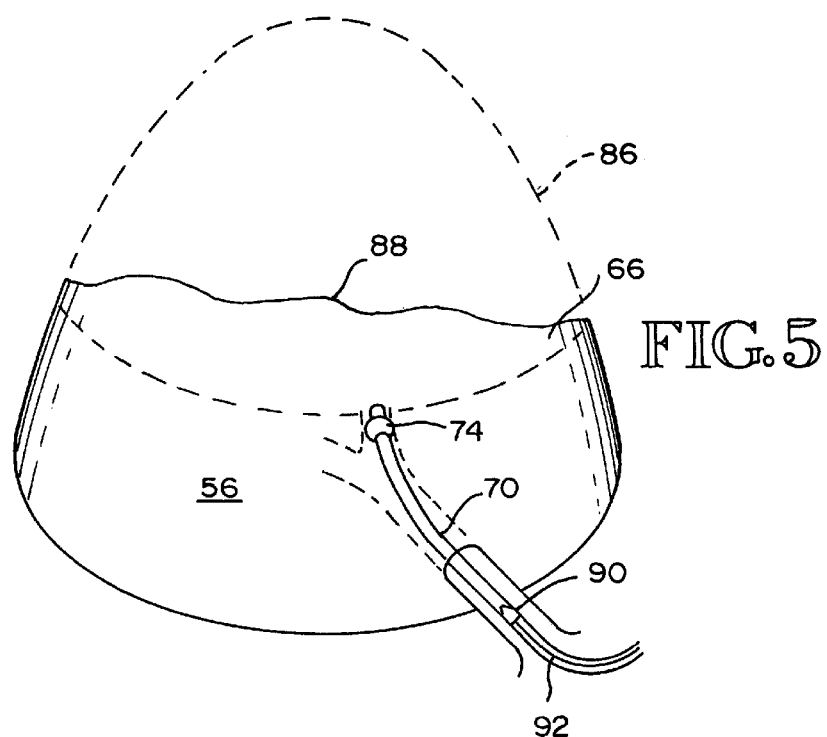
FIG. 5 is a perspective view, to an enlarged scale, illustrating the guiding of an obstructing member through the conduit for sealing a lung portion in accordance with the present invention.

Referring now to FIG. 5, here it may be seen that the lung portion 66, due to the vacuum pulled by the pump 80 and catheter 70 of FIG. 3, has collapsed from its initial state indicated by the dashed line 86 to the solid line 88. With the lung portion 66 thus collapsed, and while the lung portion 66 is collapsed, an obstructing member 90 is guided through the main channel of the conduit 70 by a stylet wire 92. This may be seen in greater detail in FIG. 6. As will be seen hereinafter with specific reference to FIGS. 8–13, the obstructing or sealing member 90 is formed of resilient or collapsible material to enable the obstructing member 90 to be fed through the conduit 70 in a collapsed state. The stylet 92 is used to push the obstructing member 90 to the end 77 of the catheter 70 for placing the obstructing member 90 within the air passageway 50 adjacent to the lung portion 66 to be permanently collapsed.

Figure 7:
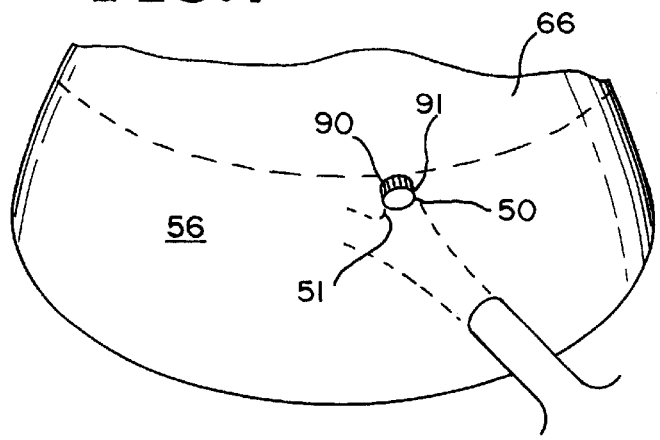
FIG. 7 is a perspective view, partly in section, and to an enlarge scale, illustrating an obstructing member positioned in an air passageway for sealing the lung portion.

FIG. 7 illustrates the obstructing or sealing member in place within the air passageway 50. The sealing member 90 has expanded upon placement in the air passageway 50 to seal the air passageway 50. This causes the lung portion 66 to be maintained in a permanently collapsed state.

More specifically, the obstructing member 90 has an outer dimension 91 when expanded to enable continuous contact with the air passageway inner dimension 51. This seals the air passageway upon placement of the obstructing member 90 in the air passageway 50 for maintaining the lung portion 66 in the collapsed state.

Alternatively, the vacuum need not be pulled in the lung portion 66. Rather, the lung portion 66, in accordance with a further embodiment of the present invention, may be collapsed by sealing the air passageway 50 with the obstructing member 90. Over time, the air within the lung portion 66 will be absorbed by the body to result in the collapse of lung portion 66. In accordance with this embodiment of the present invention, the obstructing member 90 may be placed in the air passageway 50 by utilizing catheter 70 as previously described but without pulling a vacuum or employing the inflatable sealing member 74.

Figure 8:
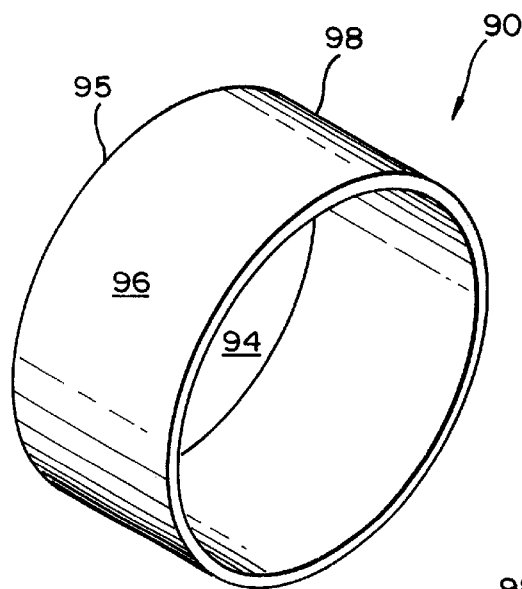
FIG. 8 is a perspective view, to an enlarged scale, of an obstructing member configured in accordance with the present invention.

Referring now to FIG. 8, it illustrates the ceiling or obstructing member 90 in greater detail. The obstructing member 90 has a hollow cylindrical configuration. More specifically, the obstructing member 90 includes a generally circular base 94 having an outer periphery 95. The obstructing member 90 further includes a circumferential generally cylindrical sidewall 96 which extends from the outer periphery 95 of the base 94. The generally cylindrical sidewall 96 has an outer surface 98 which defines the outer periphery 91 of the obstructing member as illustrated in FIG. 7.

Figure 6:
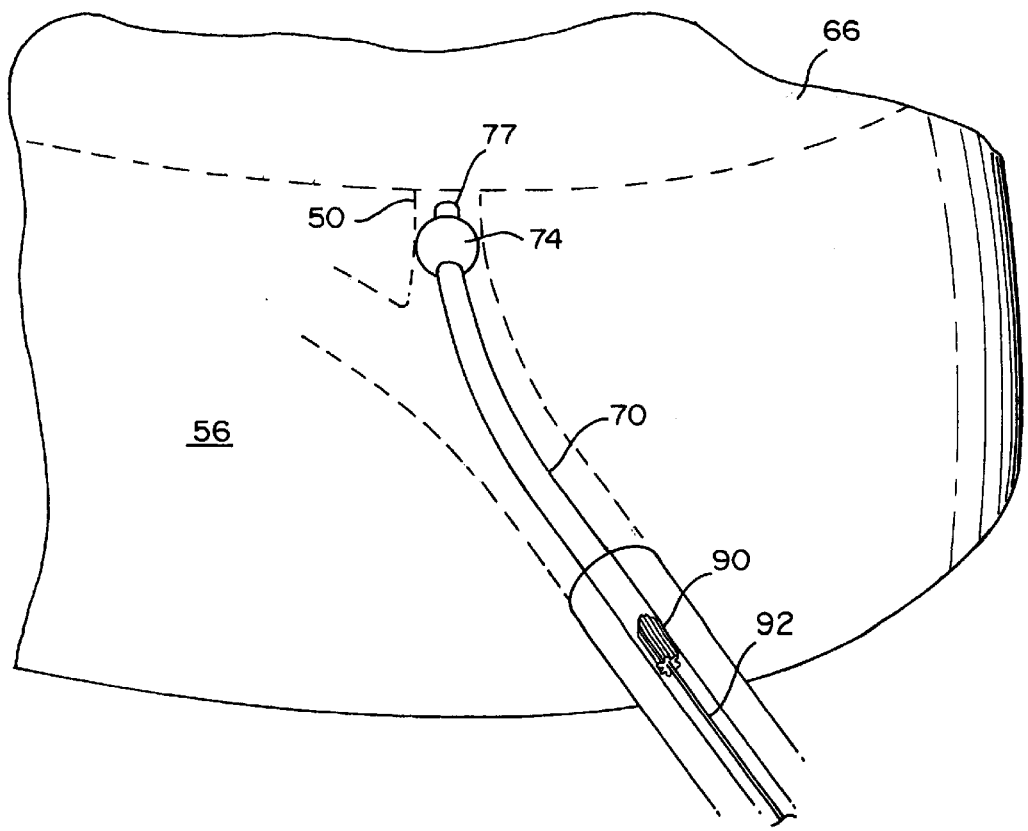
FIG. 6 is a partial exploded view of FIG. 5.

As previously mentioned, the obstructing member 90 is formed of resilient material. For example, the obstructing member 90 may be formed from silicone rubber. This renders the obstructing member 90 collapsible as illustrated in FIGS. 5 and 6 for feeding the obstructing member 90 through the catheter 70 and causing the obstructing member 90 to expand when placed in the air passageway 50 for sealing the air passageway.

Figure 9:
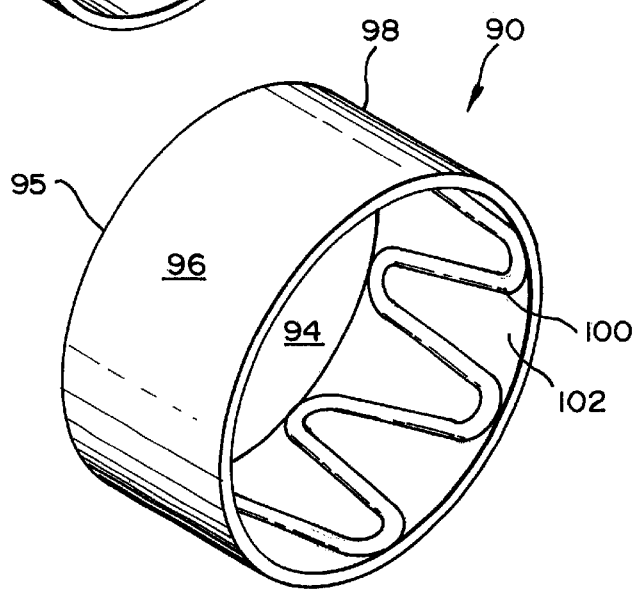
FIG. 9 is a perspective view, to an enlarged scale, of the obstructing member of FIG. 8 having a reinforcing rib.

FIG. 9 illustrates the obstructing member 90 as described with respect to FIG. 8 but, in addition, includes an inner resilient reinforcement rib 100. The reinforcement rib 100 has a generally serpentine configuration and is in contact with the inner generally cylindrical surface 102 of the obstructing member 90. The reinforcement rib 100 serves to add increased structural integrity to the obstructing member 90. In addition, the base 94, the generally cylindrical sidewall 96, and the resilient reinforcement rib 100 are all collapsible. The reinforcement rib 100, when the obstructing member 90 is positioned in place within the air passageway 50, forces the cylindrical sidewall 96 radially outwardly to form the generally circular base 94 and the circumferential generally cylindrical sidewall 96.

Figure 10:
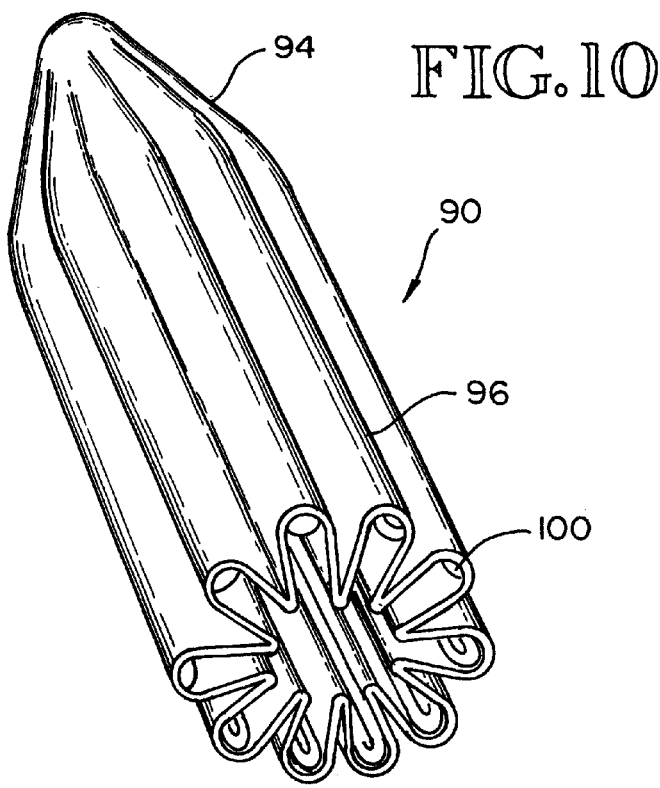
FIG. 10 is a perspective view, to an enlarged scale, illustrating the obstructing member of FIG. 6 in a collapsed condition in accordance with further aspects of the present invention.

FIG. 10 illustrates the obstructing member 90 in its fully collapsed state. Here it may be seen that the base 94, when collapsed, is generally conically shaped to assist in the placement of the collapsed obstructing member in the main channel of the conduit. Also, as can be clearly seen in FIG. 10, the resilient reinforcing rib 100 is collapsed and ready to expand the obstructing member 90 by forcing the cylindrical sidewall 96 radially outwardly.

Figure 11:
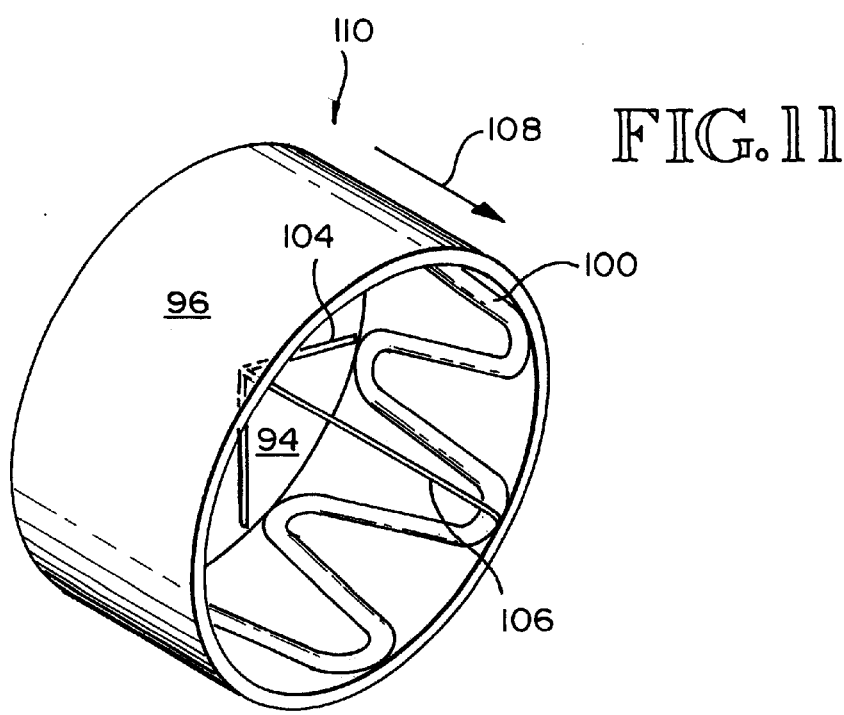
FIG. 11 is a perspective view, to an enlarged scale, of another obstructing member embodying the present invention in the form of a one-way valve.

Referring now to FIG. 11, it shows, in accordance with a further aspect of the present invention, an obstructing member 110 which is similar to the previously described obstructing member 90 but which includes a one-way valve. More specifically, the obstructing member 110 includes the generally circular base 94, the generally cylindrical sidewall 96, and the reinforcement rib 100. In addition, the base 94 is slit as illustrated at 104 to form a valve structure. A tether 106 is connected between the reinforcement rib 100 and the base 94. Hence, when positioned in the air passageway 50, the one-way valve structure of the obstructing member 110 permits air to flow in the direction indicated by the arrow 108 but precludes airflow in the opposite direction. Hence, when the obstructing member 110 is placed in the air passageway 50, it is so placed in accordance with this aspect of the present invention that it permits air to be exhaled from the lung portion to be collapsed but precludes air from being inhaled into the lung portion to be collapsed.

The one-way valve obstructing member 110 may be utilized in accordance with the embodiment wherein a vacuum is pulled within the lung portion to be collapsed or in accordance with the alternative embodiment wherein the air passageway is obstructed without the pulling of a vacuum in the lung portion to be collapsed. Because the one-way valve obstructing member 110 permits exhaled air to flow therethrough, the lung portion to be collapsed will be collapsed more quickly due to the reduction in residual air within the lung portion to be collapsed.

Figure 12:
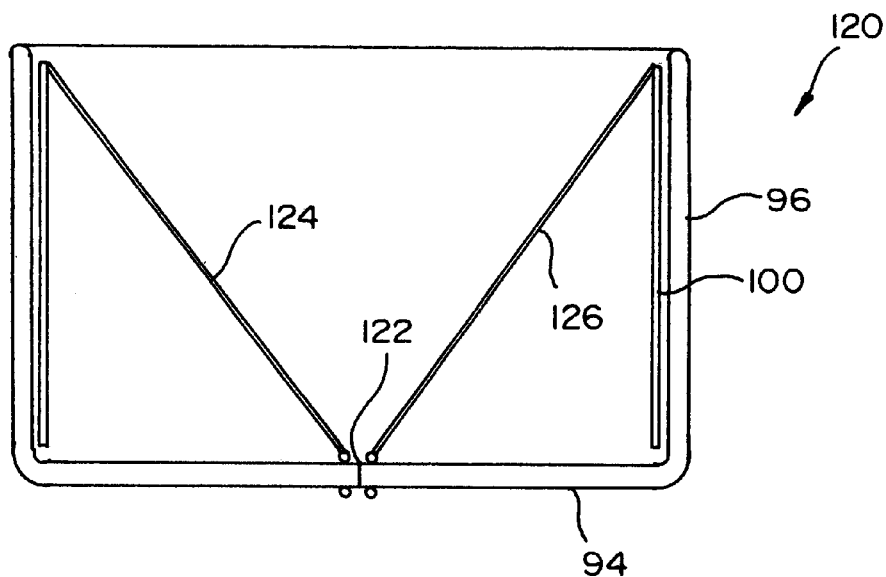
FIG. 12 is a sectional view, to an enlarged scale, of another one-way valve obstructing member embodying the present invention in a closed position.
Figure 13:
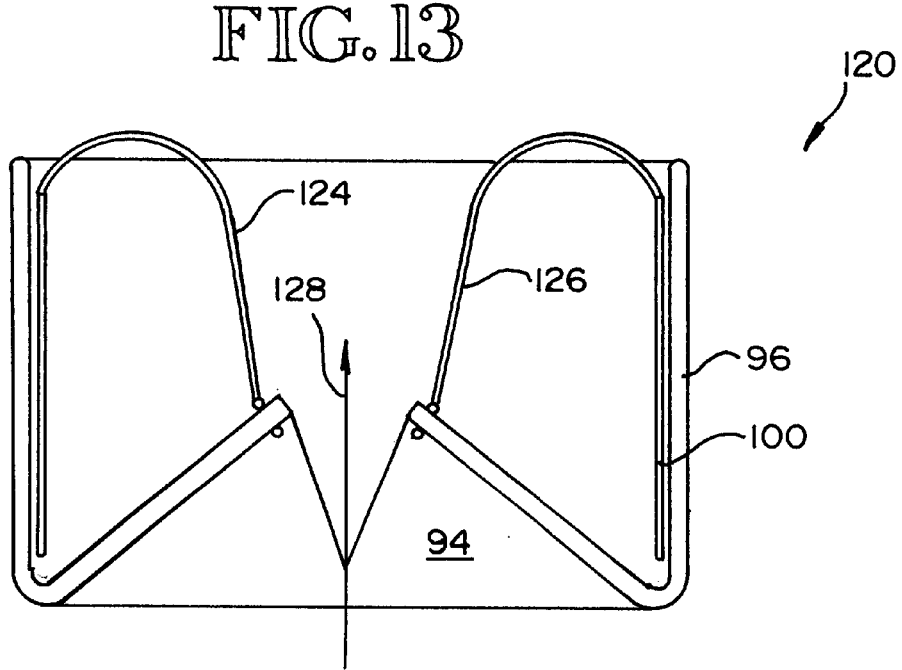
FIG. 13 is a sectional view, to an enlarged scale, of the one-way valve of FIG. 12 illustrated in an open condition.

Referring now to FIGS. 12 and 13, they illustrate another one-way valve obstructing member 120 which may be utilized in accordance with the present invention. Like the previous obstructing members, the one-way valve obstructing member 120 includes a generally circular base 94 and a circumferential generally cylindrical sidewall 96. The obstructing member 120 further includes the reinforcement rib 100. To form the valve, the base 94 includes a slit 122. On either side of the slit 122 is a tether 124 and 126 which extend to the resilient reinforcement rib 100. As a result, the one-way valve structure opens to air flow in the direction indicated by arrow 128 but precludes air flow in the opposite direction. The one-way valve obstructing member 120 may thus be employed in the same manner as the one-way valve 110 as described with reference to FIG. 11.

As can thus be seen from the foregoing, the present invention provides a device, system, and method for treating COPD by lung volume reduction. The lung volume reduction is achieved through the permanent collapsing of one or more lung portions, or lobes, or portions of lobes. The foregoing is achieved without surgery. Following the treatment, the lung tissue within the thorax will occupy a lesser volume than previously occupied providing room for the diaphragm to assume its arcuate state to assist in normal breathing and to achieve the benefits of lung volume reduction.

While particular embodiments of the present invention have been shown and described, modifications may be made, and it is therefore intended in the appended claims to cover all such changes and modifications which fall within the true spirit and scope of the invention.

What is claimed is:

1. A bronchial sub-branch obstruction device for reducing the size of a lung comprising an obstructing member dimensioned for insertion into a bronchial sub-branch communicating with a portion of the lung to be reduced in size, the obstructing member having an outer dimension which is so dimensioned as to make continuous contact with an inner dimension of the bronchial sub-branch to seal the bronchial sub-branch upon placement in the bronchial sub-branch, to preclude normal function of the lung portion, and to collapse the portion of the lung for reducing the size of the lung, wherein the obstructing member is a one-way valve to permit exhaled air to flow from the lung portion while precluding inhaled air from flowing into the lung portion.

2. The device of claim 1 wherein the obstructing member is formed of resilient material so as to be collapsible for initial insertion into the bronchial sub-branch in a collapsed condition and releasable to define the outer dimension upon placement in the bronchial sub-branch.

3. The device of claim 1 wherein the obstructing member includes a generally circular base having an outer periphery and a circumferential generally cylindrical sidewall extending from the outer periphery of the base, the generally cylindrical sidewall having an outer surface defining the outer dimension.

4. The device of claim 3 wherein the obstructing member is formed of resilient material.

5. The device of claim 4 wherein the obstructing member is formed of silicone rubber.

6. The device of claim 4 wherein the obstructing member sidewall includes an inner generally cylindrical surface and wherein the obstructing member includes a resilient reinforcement rib in contact with the inner generally cylindrical surface.

7. The device of claim 6 wherein the reinforcement rib has a serpentine configuration.

8. The device of claim 6 wherein the base, the generally cylindrical sidewall, and the resilient reinforcement rib of the obstructing member are all collapsible and wherein the resilient reinforcement rib forces the cylindrical sidewall radially outwardly when the obstructing member is positioned in the air passageway to form the generally circular base and circumferential generally cylindrical sidewall.

9. A bronchial sub-branch obstruction system for reducing the size of a lung comprising:
   a conduit configured to be passed down a trachea, into a bronchus communicating with the trachea, and into a bronchial sub-branch communicating the bronchus with a lung portion to be reduced in size; and
   an obstructing member so dimensioned as to be guidable through the conduit and placed in the bronchial sub-branch to seal the bronchial sub-branch, to preclude normal function of the lung portion, and to collapse the lung portion, wherein the obstructing member is a one-way valve to permit exhaled air to flow from the lung portion while precluding inhaled air from flowing into the lung portion.

10. The system of claim 9 wherein the obstructing member is formed of resilient material so as to be collapsible for initial insertion through the conduit into the bronchial sub-branch in a collapsed condition and releasably expandable so as to be dimensioned to seal the bronchial sub-branch.

11. The system of claim 9 wherein the obstructing member includes a generally circular base having an outer periphery and a circumferential generally cylindrical sidewall extending from the outer periphery of the base, the generally cylindrical sidewall having an outer surface for continuous engagement with the bronchial sub-branch.

12. The system of claim 11 wherein the obstructing member is formed of resilient material.

13. The system of claim 12 wherein the obstructing member is formed of silicone rubber.

14. The system of claim 12 wherein the obstructing member sidewall includes an inner generally cylindrical surface and wherein the obstructing member includes a resilient reinforcement rib in contact with the inner generally cylindrical surface.

15. The system of claim 14 wherein the reinforcement rib has a serpentine configuration.

16. The system of claim 14 wherein the base, the generally cylindrical sidewall, and the resilient reinforcement rib of the obstructing member are all collapsible and wherein the resilient reinforcement rib forces the cylindrical sidewall radially outwardly when the obstructing member is positioned in the bronchial sub-branch to form the generally circular base and circumferential cylindrical sidewall.

17. A system for reducing the size of a lung comprising:
   a conduit configured to be passed down a trachea, into a bronchus communicating with the trachea, and into an air passageway communicating the bronchus with a lung portion to be reduced in size;
   an obstructing member configured to be guided through the conduit into the air passageway for placement in the air passageway and sealing the air passageway for collapsing the lung portion; and
   a vacuum source for pulling a vacuum in the lung portion prior to placement of the obstructing member.

18. The system of claim 17 wherein the vacuum source is configured for being coupled to the conduit for pulling the vacuum through the conduit.

19. The system of claim 17 wherein the conduit has an outer dimension smaller than an inner dimension of the passageway, and wherein the system further includes sealing means for sealing between the conduit outer dimension and the air passageway inner dimension.

20. The system of claim 19 wherein the sealing means comprises an inflatable member.

21. The system of claim 20 wherein the conduit includes a first channel for guiding the obstructing member and a second channel for inflating the inflatable member.

22. A bronchial sub-branch obstruction device for reducing the size of a lung comprising an obstructing member dimensioned for insertion into a bronchial sub-branch communicating with a portion of the lung to be reduced in size, the obstructing member having an outer dimension which is so dimensioned as to make continuous contact with an inner dimension of the bronchial sub-branch to seal the bronchial sub-branch upon placement in the bronchial sub-branch to preclude air from being exhaled from the lung portion and inhaled into the lung portion for collapsing the portion of the lung and reducing the size of the lung, wherein the obstructing member is a one-way valve to permit exhaled air to flow from the lung portion while precluding inhaled air from flowing into the lung portion.

23. A bronchial sub-branch obstruction system for reducing the size of a lung comprising:

a conduit configured to be passed down a trachea, into a bronchus communicating with the trachea, and into a bronchial sub-branch communicating the bronchus with a lung portion to be reduced in size; and an obstructing member so dimensioned as to be guidable through the conduit and placed in the bronchial sub-branch to seal the bronchial sub-branch to preclude air from being exhaled from the lung portion and inhaled into the lung portion and to collapse the lung portion, wherein the obstructing member is a one-way valve to permit exhaled air to flow from the lung portion while precluding inhaled air from flowing into the lung portion.

* * * * *